United States Patent [19]

Woessner et al.

[11] 4,138,583

[45] Feb. 6, 1979

[54] CYCLOALKENYL ANALOGUES OF PROSTAGLANDIN F

[75] Inventors: Warren D. Woessner; William G. Biddlecom; Henry C. Arndt, all of Madison; George P. Peruzzotti, Middleton; Charles J. Sih, Madison, all of Wis.

[73] Assignee: Miles Laboratories, Inc., Elkhart, Ind.

[21] Appl. No.: 803,611

[22] Filed: Jun. 6, 1977

Related U.S. Application Data

[60] Division of Ser. No. 624,099, Oct. 20, 1975, Pat. No. 4,066,834, which is a continuation-in-part of Ser. No. 436,222, Jan. 24, 1974, abandoned, which is a division of Ser. No. 383,670, Jul. 30, 1973, abandoned.

[51] Int. Cl.$^2$ ............................................. C07C 177/00
[52] U.S. Cl. ..................................... 560/118; 562/500
[58] Field of Search .................... 560/118; 260/514 D

[56] References Cited

FOREIGN PATENT DOCUMENTS 7410185  2/1975  Netherlands ........................... 260/468

Primary Examiner—Robert Gerstl
Attorney, Agent, or Firm—Myron B. Sokolowski; Jerome L. Jeffers

[57] ABSTRACT

Analogues of prostaglandins A, E, and F in which the $C_{13}$–$C_{20}$ chain of the natural prostaglandins is replaced by a cycloalkenyl or a hydroxycycloalkenyl moiety such that vinylene radical and the hydroxyl group of the ring respectively retain their natural sequential positions at $C_{13}$–$C_{14}$ and $C_{15}$, inhibit aggregation of platelets in vitro and exhibit useful cardiovascular activity in vivo.

5 Claims, No Drawings

CYCLOALKENYL ANALOGUES OF PROSTAGLANDIN F

REFERENCE TO PRIOR APPLICATION

This is a division, of application Ser. No 624,099, filed 20 Oct. 1975 now Pat. No. 4,066,834, which in turn is a continuation-in-part of U.S. Pat. Application Ser. No. 436,222, filed on Jan. 24, 1974, which in turn is a division of U.S. Pat. application Ser. No. 383,670, filed on July 30, 1973; both prior applications are abandoned.

BACKGROUND OF THE INVENTION

1. Field of the Invention

Compounds of this invention are analogues of natural prostaglandins.

Natural prostaglandins are twenty-carbon atom alicyclic compounds related to prostanoic acid which has the following structure:

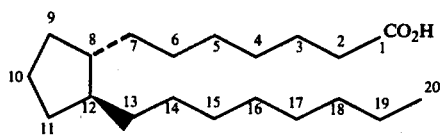

(I).

By convention, the carbon atoms of I are numbered sequentially from the carboxylic carbon atom. An important stereochemical feature of I is the trans-orientation of the side chains $C_1$–$C_7$ and $C_{13}$–$C_{20}$. In I, as elswhere in this specification, a dashed line (--) indicates projection of a covalent bond below the plane of a reference carbon atom (alpha-configuration), while a wedged line (◂) represents direction above that plane (beta-configuration). Those conventions apply to all compounds subsequently discussed in this specification.

Natural prostaglandins have the structures,

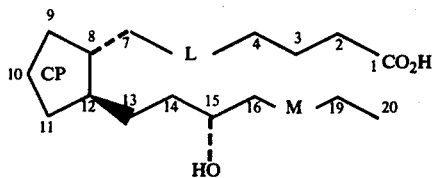

(II), in which:

L and M may be ehtylene or vinylene radicals and the five-membered ring

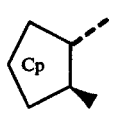

may be:

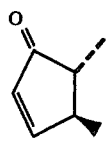 (A-class); 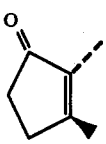 (B-class);

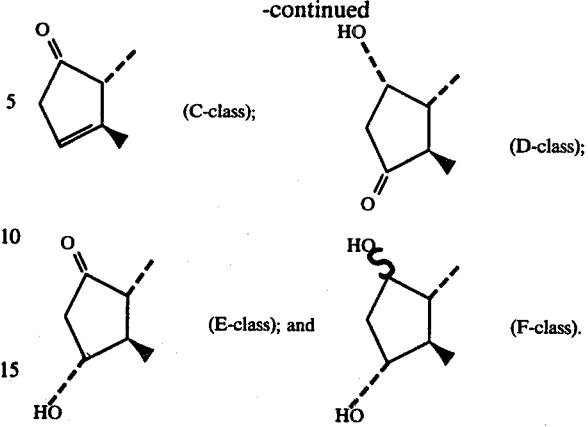

Prostaglandins are classified according to the functional groups present in the five-membered ring and the presence of double bonds in the ring or chains. Prostaglandins of the A-class (PGA) are characterized by an oxo group at $C_9$ and a double bond at $C_{10}$–$C_{11}$ ($\Delta^{10,11}$); those of the B-class (PGB) have an oxo group at $C_9$ and a double bond at $C_8$–$C_{12}$ ($\Delta^{8,12}$); compounds of the C-class (PGC) contain an oxo group at $C_9$ and a double bond at $C_{11}$–$C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the F-class (PGF) have either an alpha- or beta-directed hydroxy group at $C_9$ and an alpha-oriented group at $C_{11}$. Within each of the A, B, C, D, E, and F classes of prostaglandins are three subclassifications based upon the presence of double bonds in the side chains at $C_5$–$C_6$, $C_{13}$–$C_{14}$, or $C_{17}$–$C_{18}$. The presence of a trans-unsaturated bond only at $C_{13}$–$C_{14}$ is indicated by the subscript numeral 1; thus, for example, $PGE_1$ denotes a prostaglandin of the E-type (oxo group at $C_9$ and an alpha-hydroxyl at $C_{11}$) with a trans-double bond at $C_{13}$–$C_{14}$. The presence of both a trans-double bond at $C_{13}$–$C_{14}$ and a cis-unsaturated bond at $C_5$–$C_6$ is denoted by the subscript numeral 2; for example, $PGE_2$. Lastly, a trans-double bond at $C_{13}$–$C_{14}$, a cis-double bond at $C_5$–$C_6$ and a cis-double bond at $C_{17}$–$C_{18}$ is indicated by the subscript numeral 3 for example, $PGE_3$. The above notations apply to prostaglandins of the A, B, C, D, and F series as well, however, in the latter the alpha -orientation of the hydroxyl group at $C_9$ is indicated by the subscript Greek letter $\alpha$ after the numerical subscript. A similar convention applies to PGF molecules in which the $C_9$ hydroxy has the $\beta$-orientation. Thus, $PGF_{3\alpha}$ represents $9\alpha,11\alpha,15\alpha$-trihydroxy-5,17-cis, 13-trans-prostatrienoic acid (utilizing nomenclature based upon prostanoic acid).

It is important to note that in all natural prostaglandins there is an alpha-oriented hydroxy group at $C_{15}$. In the Cahn-Ingold-Prelog system of defining sterochemistry, that $C_{15}$ hydroxyl group is in the S-configuration.

11-Deoxy derivatives of PGE and PGF molecules do not occur as such in nature, but constitute a class of compounds which possess biological activity related to the parent compounds. Formula II represents 11-deoxy PGE and PGF compounds when

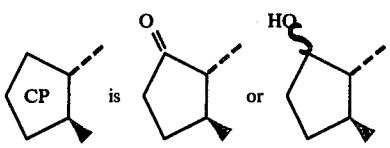

respectively.

I.U.P.A.C. nomenclature of prostaglandins designates the carboxylic side chain as the parent compound; for example, PGF$_{3\alpha}$ is 7-{3α,5α-dihydroxy-2β-[(3S)-3-hydroxy -trans-1, cis-5-oxtenyl]-1α-cyclopentyl)-cis-5-heptenoic acid.

Recent research indicates that prostaglandins are ubiguitous in animal tissues and that prostaglandins, as well as their synthetic analogues, have important biochemical and physiological effects in mammalian endocrine, reproductive, central and peripheral nervous, sensory, gastro-intestinal, hematic, respiratory, cardiovascular, and renal systems.

In mammalian endocrine systems, experimental evidence indicates prostaglandins are involved in the control of hormone synthesis or release in hormone-secretory glands. In rats, for example, PGE$_1$ and PGE$_2$ increase release of growth hormone while PGA$_1$ increased synthesis of that hormone. In sheep, PGE$_1$ and PGF$_{1\alpha}$ inhibit ovarian progesterone secretion. Ina variety of mammals, PGF$_{1\alpha}$ and PGE$_{2\alpha}$ act as luteolytic factors. In mice, PGE$_1$, PGE$_2$, PGF$_{1\alpha}$ and PGE$_{1\beta}$ increase thyroid activity. In hypophysectomized rats, PGE$_1$, PGE$_2$ and PGF$_{1\alpha}$ stimulate steroidogenesis in the adrenal glands.

In the mammalian male reproductive systen, PGE$_1$ contracts the smooth muscle of the vas deferens. In the female reproductive system, PGE and PFG$_{60}$ compounds contract uterine smooth muscle. In general, PGE, PGB and PGA compounds relax in vitro human uterine muscle strips, while those of the PGF$_{60}$ class contract such isolated preparations. PGE compounds in general promote fertility in the female reproductive system while PGF$_{2\alpha}$ has contragestational effects. PGF$_{2\alpha}$ also appears to be involved in the mechanism of menstruation. In general, PGE$_2$ exerts potent oxytocic effects in inducing labor, while PGF$_{2\alpha}$ induces spontaneous abortions in early pregnancy.

PGF$_{60}$ and PGE compounds have been isolated from a variety of nervous tissue and they seem to act as neurotransmitters. PGE$_1$ retards whereas PGF$_{2\alpha}$ facilitates transmission in motor pathways in the central nervous system. It has been reported that PGE$_1$ and PGE$_2$ inhibit transmitter release from adrenergic nerve endings in the guinea pig.

Prostaglandins stimulate contraction of gastrointestinal smooth muscle in vivo and in vitro. In dogs, PGA$_1$, PGE$_1$ and PGE$_2$ inhibit gastric secretion. PGA$_1$ exhibits similar activity in man.

In most mammalian respiratory tracts, compounds of the PGE aND PGF class relax in vitro preparations of tracheal smooth muscle. In that preparation, PGE$_1$ and PGE$_2$ relax while PGF$_{2\alpha}$ contracts the smooth muscle. PGE and PGF compounds are normally found in the human lung, and it is postulated that some cases of bronchial asthma involve an imbalance in the production or metabolism of those compounds.

Prostaglandins are involved in certain hematic mechanisms in mammals. PGE$_1$, for example, inhibits thrombogenesis in vitro through its effects on blood platelets. In a variety of mammalian cardiovascular systems, compounds of the PGE and PGA class are vasodilators whereas those of the PGF$_{60}$ class are vasoconstrictos, by virtue of their action on vascular smooth muscle.

Prostaglandins are naturally found in the kidney and reverse experimental and clinical renoprival hypertension.

The clinical implications of prostaglandins and their analogues are far-ranging and include, but are not limited to the following: In obstetrics and gynecology, they may be useful in fertility control, treatment of menstrual disorders, induction of labor, and correction of hormone disorders; in gastroenterology, they may be useful in the treatment of peptic ulcers and various disorders involving motility, secretion, and absorption in the gastrointestinal tract; in the respiratory area, they may be beneficial in the therapy of bronchial asthma and other diseases involving bronchoconstriction; in hematology, they may have utility as anti-clotting agents in diseases such as venous thrombosis, thrombotic coronary occlusion and other diseases involving thrombi; in circulatory diseases they may have therapeutic utility in hypertension, peripheral vasopathies, and cardiac disorders.

For a more complete review of chemical, physiological and pharmacological aspects of the prostaglandin, consult the following references: The Prostaglandinc, Vol. I., P. Ramwell, Ed., New York, Plenum Press, 1973; Ann. N.Y. Acad. Sci., 180: 1-568 (1971); and Higgins and Braunwald, J. Am. Med. Assn., 53: 92–112 (1972.).

SUMMARY

Prostaglandin analogues having structural formula III are the subject matter of this invention:

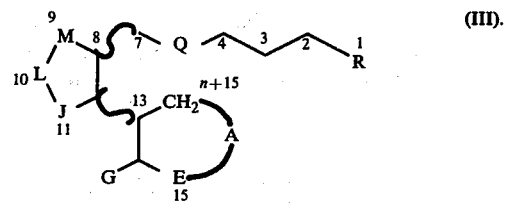

In III:

A is an alkylene bridge containing n methylene groups where n is an integer having a value of from 1 to 8; A therefore is a methylene, ethylene, 1,1-dimethylethylene (such that the dimethylsubstituted carbon atom is C$_{17}$ in the cycloalkenyl moiety), trimethylene, tetramethylene, pentamethylene, hexamethylene, heptamethylene, or octamethylene radical;

E is a methylene, α-hydroxymethylene, or a β-hydroxymethylene radical;

G is a hydrogen atom or a methyl group;

J is a methylene, α-hydroxymethylene, β-hydroxymethylene, or a methine radical such that J is methine only when L is methine also;

L is a methylene or a methine radical but is methine only when J is methine;

M is a carbonyl group, an α-hydroxymethylene or a β-hydroxymethylene group;

Q is either an ethylene or a vinylene radical; and

R is a carbinol, carboxyl, carbomethoxy, or carbethoxy group.

Numerical designation of carbon atoms in III follows the convention established for the natural prostaglandins. Thus when R is a carboxy or a carbinol group, the carbon atom in such group is the first carbon atom ($C_1$) in the structure. When R is a carbalkoxy group, however, the carbon atom of the oxo radical is the first carbon atom in the structure:

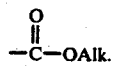  (1)

The novel structural feature of III is the replacement of the $C_{13}$–$C_{20}$ chain of the natural prostaglandins by a cycloalkenyl moiety such that the $C_{13}$–$C_{14}$ vinylene radical and the $C_{15}$ hydroxyl group (except where a given species) of II is a 15-deoxy analogue) retain their sequential positions relative to atoms $C_1$–$C_{12}$ of the prostaglandin structure. Thus, by the way of illustration, 2α-(6'-carboxyhexyl)-3β-(3"-α-hydroxy-cyclohexen-1-yl)-cyclopent-4-enone,

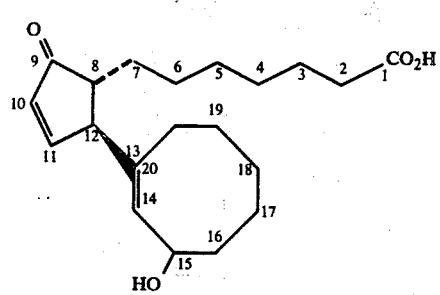

is a compound represented by III that is an analogue to $PGA_1$,

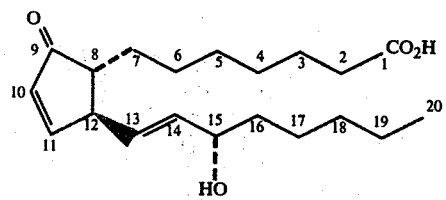

Note, however, that the cycloalkenyl moiety of III is not limited to a cyclooctenyl group but can contain from 5 to 12 carbon atoms which comprise the ring.

Formula III encompasses preferred subgeneric structures representing analogues of the A-, E-, and F-classes of the natural prostaglandins. Thus when G is hydrogen, both J and L are methine radicals and M is a carbonyl group, III denotes analogues of the A-family of prostaglandins:

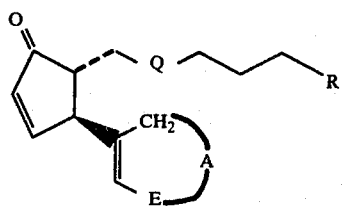  (IIIa).

When J is α- or β-hydroxymethylene, L is methylene M is carbonyl, III represents preferred analogues of the E-class of prostaglandins:

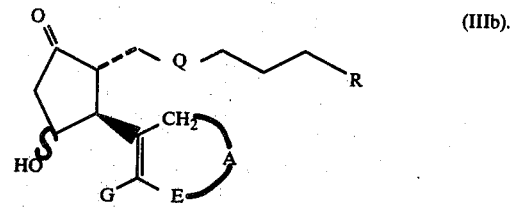  (IIIb).

When G is hydrogen, J and L are methylene, and M is carbonyl, III includes preferred analogues of 11-deoxy-derivatives of the E- family:

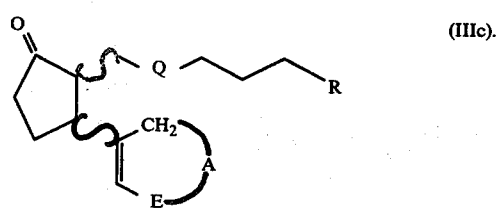  (IIIc).

When G is hydrogen, both J and M are either α- or β-hydroxy-methylene, L is methylene and Q is ethylene, III represents preferred analogues of $PGF_{1α}$ and $PGF_{1β}$:

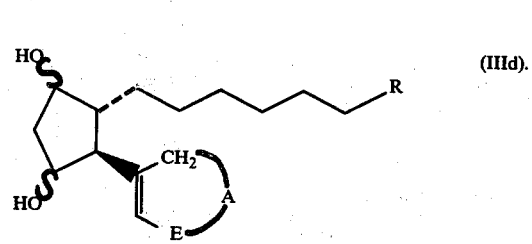  (IIId).

Preparation of analogues having structure III proceeds by a modification of the synthesis reported by Sih et al. (J. Am. Chem. Soc., 95: 1676 [1973]). The former is outlined in Table A.

In Table A, rection of the 1-bromo-cyclo-alk-1-ene (IVa) or 1bromo-3-ethoxyethoxy-cyclo-alk-1-ene (IVb) with: t-butyl-lithium (V), hexamethylphosphorous triamide (VI); and the 2-substituted-cyclopent-2-enone (VIIa), 2-substituted -4-(tetrahydropyranox-1yl)-cyclopent-2-enone (VIIb), or 1,4-(ditetrahydropyranox1-yl)-2-substituted-cyclopent-2-ene (VIIc) at from about −70° C. to about −50° C. in ether yields the corresponding 4-(1-cycloalken-1yl) or 4-(3-ethoxyethoxy-1-cycloalken-1-yl) intermediate, VIII. Treatment of the latter with standard reagents under standard conditions to remove the ethoxyethoxy or tetrahydropyranoxy groups ($CH_3CO_2H$; THP; $H_2$) or to hydrolyze ester groups ($H_2O$; THF; NaOH) where applicable provides compound III.

TABLE A
SYNTHETIC PATHWAY FOR PREPARATION OF COMPOUNDS III

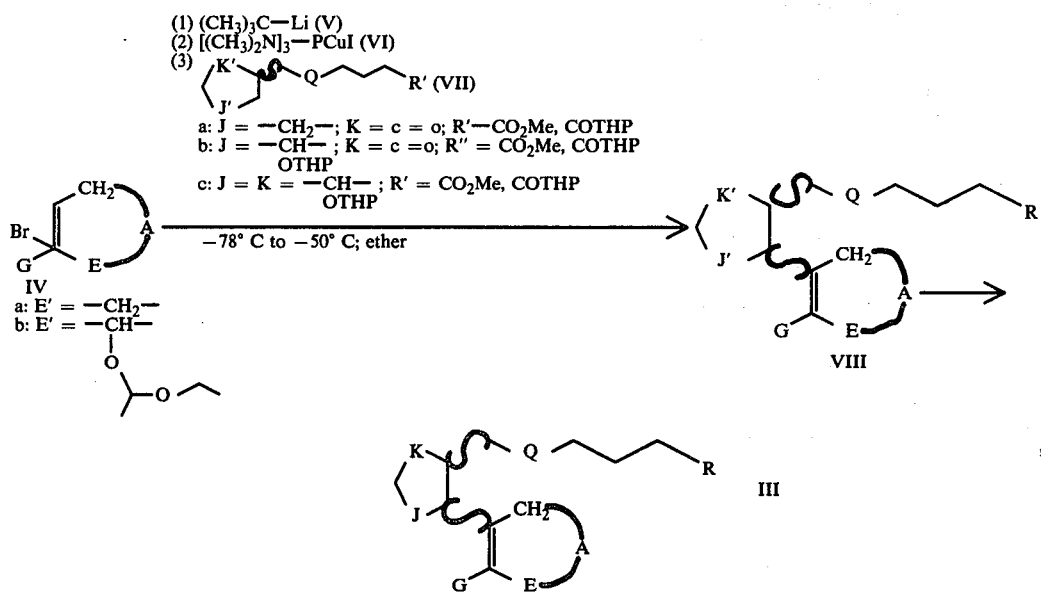

TABLE B
Synthetic Pathway For Preparation Of Starting Materials IVa

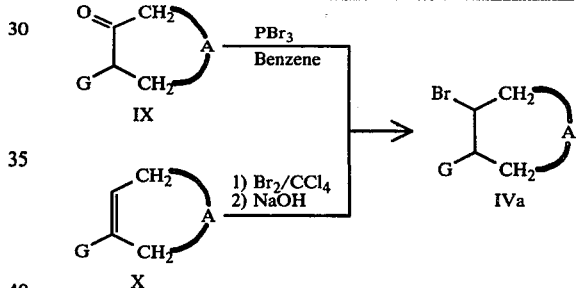

CuI (inorg. Synth., 7:9 [1963]) to 177 g KI in 135 ml H$_2$O and stir with arbronted charcoal (NORITE ®); (2) filter the resulting solution through infusorial earth (CELITE ®) and add 14.5 g (0.089 mol) of hexamethylphosphorous triamide (commerically available) under argon atmosphere; (3) filter and wash with aqueous KI and with H$_2$O; (4) dissolve the product in dry ether, filter, remove the ether in vacuo to obtain 13.05 g of VI: NMR(CDCl$_3$) - δ2.65 s. compounds VII are prepared according to reported methods: Sih et al., J. Am. Chem. Soc., 95:1076 (1973); and Heather et al, Tetrahedron Letters, No. 25, 2313 (1973). Examples of VII which are employed in the synthesis of compounds III are: 2-(6'-carbomethyoxyhexyl)-4-tetrahydropyranoxy-cyclopent-2-enone; 2-(6'-carbethoxyhexyl)-4-tetrahydropyranoxy-cyclopent-2-onone; 2-(7'-tetrahydropyranoxyhexyl)-4-tetrahydropyranoxy-cyclopent-2-onone; 2-(6'-carbomethoxy-cis-2'-hexenyl) -4-tetrahydropyranoxy-cyclopent-2-onone; 2-(6'-carbethoxy-cis-2'-hexenyl)-4-tetrahydropyranoxy-cyclopent-2-onone; 2-(7'-tetrahydropyranoxyhexyl-cis-2'-hexenyl)-4-tetrahydropyranoxy-cyclopent-2-onone; 1,4-di(tetrahydropyranoxy)-2-(6'-carbomethyoxyhexyl)-cyclopent-2-enone; 1,4-di(tetrahydropyranoxy)-2-(6'-carbethoxyhexyl)-cyclopent-2-enone; 1,4-di-(tetrahydropyranoxy)-2-(7'-tetrahydropyranoxy)-cyclopent-2-enone; 1,4-di(tetrahydropyranoxy-2-(6'-carbomethoxy-cis-2-hexenyl)-cyclopent-2-enone; 1,4-di(tetrahydropyranoxy)-2-(6'-carbethoxy-cis-2-hexenyl)-cyclopent-2-enone; 1,4-di-(tetrahydropyranoxy)-2-(7'-tetrahydropyranoxy-cis-2-hexenyl)-cyclopent-2-enone.

Preparation of starting materials IV may proceed by a variety of pathways, summarized in Tables B and C.

Tables B and C present the pathway for synthesis of materials IVa and IVb, those pathways are known to the art and reported in the following references:- Newman et al., J. Org. Chem., 28: 1851 (1963); Montgomery et al., J. Am. Chem. Soc. 87: 1917 (1965); Org. Snyth., Coll. Vol. I, 209 (1943); Org. Synth., Coll. Vol. II, 171 (1941); Bull. Soc. Chim. France, 3097 (1970); and Whitsides et al., J. Am. Chem. Soc., 93: 1379 (1971).

In Table B, IX represents a cycloalkanone or a 2-methyl-cycloalkanone having from 5 to 12 carbon atoms in the ring; in IX, G obviously is a hydrogen atom or a methyl group; and A is a methylene, ethylene, 1,1-dimethylethylene, trimethylene, tetramethylene, pentamethylene, hexamethylene, hepamethylene, or octamethylene radical as defined in III. Formula IX, therefore, represents, among other compounds cyclopentanone, 2-methylcyclopentanone, cyclohexanone, 5,5-dimethylcyclohexanone, cycloheptanone, cyclooctanone, cyclononanone, cyclodecanone, cycloundecanone, or cyclododecanone. Treatment of IX with phosphorous tribromide in benzene under conditions recited in the prior art references yields the corresponding 1-bromocycloalk-1-ene or the 1-bromo-2-methyl-cycloalk-1-ene, Iva. Alternately, compounds X may be used as starting materials; in X, symbols A and G have the same meaning as defined for III and IX. compounds X, therefore, include, among others, cyclopent-1-ene, 2-methylcyclopent-1-ene, cyclohex-1-ene, 5,5-dimethyl-1-cyclohex-1-ene, cyclohept-1-ene, cyclooct-1-ene, cyclonon-1-cyclodec-1-ene, cycloundec-1-ene, or cyclododec-1-ene. Reaction of X with bromine in chloroform under conditions reported in the cited art and subsequent treatment with NaHO provides in corresponding compounds IVa. Either pathway provides the following examples of IVa: 1bromo-cyclopent-1-ene, 1-bromo-cyclohex-1-ene; 1-bromo-2-methyl-cyclohex:1-ene; 1-bromo-cyclohept-1-ene; 1-bromo-cyclooc-1-tene; 1bromo-cyclonon-1-ene; 1-bromo-cyclodec-1-ene; 1-bromo-cyclo-undec-1-ene; or 1-bromo-cyclodidec-1-ene.

Table C outlines the reaction sequence involved in the synthesis of starting compounds IVb. reaction of 1,3-cycloalkadione or a 2-methyl-1,3-cycloalkadione, XI, with phosphorous tribromide in benzene under conditions stated in the cited references provides the corresponding 3-bromo-cycloalk-2-en1-one or 2-methyl-3-bromo-cycloalk-2-ene1-one, XII. Reduction of the latter with sodium borohydride in either methanol or ethanol at about 0° C. provides a 3-bromo-cycloalk-2-en-1-ol or a 2-methyl-3-bromo-cycloalk-2-en-1-ol intermediate, XIII. Introduction of an ethoxyethoxy group under conditions utilized in the cited literature results in IVb. Starting materials XI either are available commerically or are prepared by methods known to one skilled in the art. Representative of XI are: 1,3-cyclopentadione; 2-methyl-1,3-cyclopentadione; 1,3-cyclohexadione; 5-dimethyl-1,3-cyclohexadione; 1,3-cycloheptadione; 1,3-cyclooctadione; 1,3-cyclononadione; 1,3-cyclodecadione; 1,3-cycloundecadione; 1,3-cyclododecadione. Representatives of IVb are: 1bromo-3-(ethoxyethoxy)-cyclopent-1-ene; 1-bromo-2-methyl-3-(epoxyethyoxy)-cyclopent-1-ene; 1-bromo-3-ethoxyethoxy-cyclohex-1-ene; 1bromo-3ethoxyethoxy-5-dimethyl-cyclhex-1-ene; 1-bromo-3-ethoxyethoxy-cyclophept-1-ene; 1-bromo-3-ethoxyethoxy-cyclooct-1-ene; 1-bromo-3-ethoxy-ethoxy-cyclonon-1-ene; 1-bromo-3-ethoxyethoxy-cyclodec-1-ene; 1-bromo-3-ethoxyethoxy-cycloundec-1-ene; 1-bromo-3-ethoxyethoxy-cyclododec:1-ene.

TABLE C
Synthetic Pathway For Preparation Of Starting Compound IVb

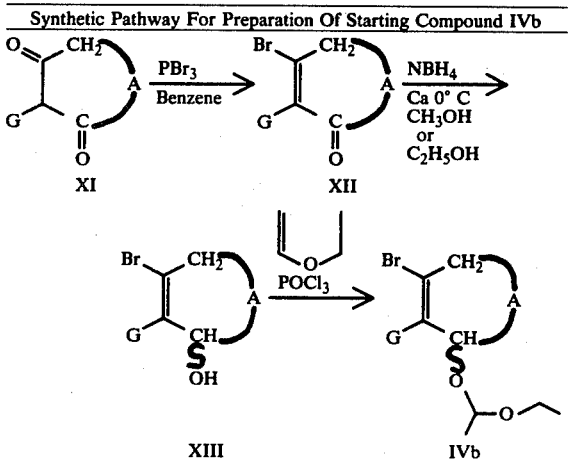

Analogues of PGA are prepared by treating corresponding analogues of PGE₁, PGE₂, 11-deoxy-PGE₁or 11-deoxy PGE₂ with acid (Anderson, N., J. Lipid Res., 10: 320 [1969]):

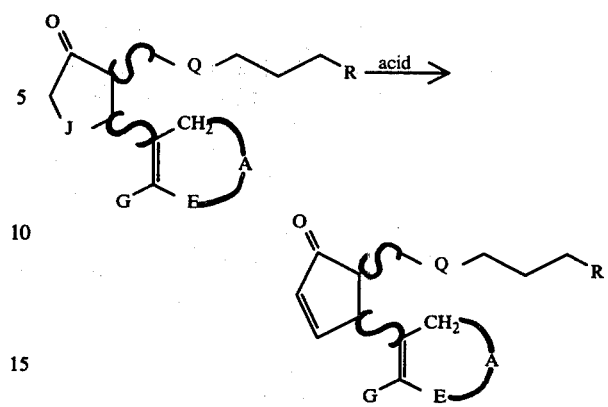

Compounds III as a genus inhibit aggregation of human plateltes in vitro, as demonstrated in following examples 25. It is that feature which distinguishes the compounds of this invention over the natural prostaglandins. Of the latter, only PGE₁ displays similar activity. Certain species of III also are antihypertensive or vasodilating agents in vivo as shown in example 25. It should be noted that the latter features are not incompatible with their activity as inhibitors of blood platelets.

DESCRIPTION OF THE PREFERRED EMBODIMENTS

Examples 1-7 are preferred embodiments of analogues of prostaglandins of the E- class and have structure IIIb, described in the preceding SUMMARY OF THE INVENTION:

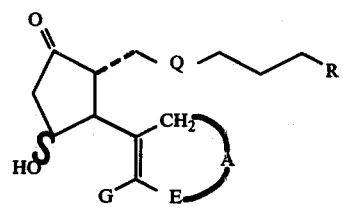

EXAMPLES 1-2:

2α-(6'Carbomethoxyhexyl)-3β(3"α-Hydroxy-Cyclohex-1-en1-yl)-4α-Hydroxycyclopentanone (TR 4082)

2α-(6'-Carbomethoxyhexyl)3"β-Hydroxy-Cyclohex-1-en-1-yl)-4α-Hydroxycyclopentanone (TR 4083)

A solution of 370 mg (2.21 mmol) of 1-bromo-3-(1'-ethoxyethoxy)cyclohex-1-ene in 12 ml of dry ether was stirred at −78° C. under argon atmosphere while a solution of t-butyllithium in pentane (2.60 ml, 4.42 mmol, 1.7 M) was added dropwise. The resulting solution was stirred for 2 hours at −78° C.; that solution then was transferred via polyethylene tubing to a mixture of copper(I)pentyne (287 mg, 2.21 mmol) in 8 ml of dry ether and 0.622 ml of dry hexamethylphosphoroustriamide; the entire reaction mixture then was cooled to −78° C. under argon atmosphere and was stirred for 30 minutes. A solution of 648 mg (2 mmol) of 2-6'-carbomethoxyhexyl)-4α-(tetrahydropyranyloxy)-cyclopent-2-enone in 4 ml of dry ether was added dropwise to that reaction mixture. The final mixture was stirred for 30 minutes at −78° C., for 90 minutes at −20° C. and for 30 minutes at 0° C. It was quenched at −20° C. by the addition of 20 ml of 20% ammonium sulfate solution and then poured into 100 ml of 20% ammonium sulfate. It then was extracted with ether (3 × 50 ml). Combined ethereal extracts were washed with 50 ml of cold 2% aqueous sulfuric acid. The wash solution again was extracted with ether (2 × 50 ml); combined extracts were filtered through infusorial earth (CELITE ®) and washed with 50 ml of saturated aqueous sodium bicarbonate and 50 ml of brine. They were dried (MgSO$_4$) and evaporated in vacuo to yield 1.037 g of a clear oil. That residue was dissolved in 10 ml of acetic acid-water-tetrahydrofuran 65:35:10) and was stirred overnight at room temperature under nitrogen. Solvent was removed by evaporation in vacuo; then residue was taken up in 50 ml of ethyl acetate-ether (1:1) and washed with 50 ml of water. The wash solution again was extracted with ethyl acetate-ether (1:1; 2 × 50 ml), and the combined extracts were washed with 50 ml of saturated aqueous sodium bicarbonate and brine. The latter were dried (MgSO$_4$) and evaporated in vacuo to yield 0.674 g of crude prostaglandin analogues. That product was purified by chromatography on silicic acid-CELITE (85:15) using benzene-ethyl acetate gradient elution to yield 143.9 mg of TR 4082 and 81.9 mg of TR 4083.

Physical Chemical Data

TR 4082 — IR (CHCl$_3$): 3600–3200, 2950, 1740cm$^{-1}$;
NMR(CDCl$_3$): δ 1.03-3.0(22H, m); 3.7(3H, s); 4.1-4.3(4H, m); and 5.65 ppm(2H, m, J=4Hz).
TR 4083 — IR(CHCl$_3$): — 3600-3200, 2950, 1740cm$^{-1}$;
NMR(CDCl$_3$): — δ1.01-2.8(22H, m): 2.7(3H, s); 3.6-4.4(4H, m); and 6.78 ppm(2H, m, J=4Hz).

EXAMPLES 3-4:

2α-(6′-Carbomethoxyhexyl)-3β-(3″ α-Hydroxy-5″,5″-Dimethyl-Cyclohex-Cyclohex-1-en-1-yl)-4α-Hydroxy-Cyclopentanone (TR 4086)

2α-(6′-Carbomethoxyhexyl)-3-β-(3″β-Hydroxy-5″,5″-Dimethyl-Cyclohex-1-en-1-yl)-4-α-Hydroxy-Cyclopentanone (TR 4087).

A solution of 610 mg (2.21 mmol) of 1-bromo-3-(1′-ethoxyethoxy)-5,5-dimethylcyclohex-1-ene in 12 ml of dry ether was stirred at −78° C. under argon atmosphere while a solution of t-butyllithium in pentane (2.60 ml, 4.42 mmol, 1.7 M) was added dropwise. That solution was stirred for 2 hours at −78° C. It was then transferred at room temperature via polyethylene tubing to a mixture of copper(I)pentyne (287 mg, 2.21 mmol) in 8 ml of dry ether and 0.622 ml of dry hexamethylphosphorous triamide; the entire reaction mixture then was cooled to −78C under argon atmosphere and was stirred 30 minutes at −78° C. A solution of 648 mg (2.0 mmol) of 2-(6′-carbomethoxyhexyl)-4α-tetrahydropyranyloxy-cyclopent-2-enone in 4 ml of dry ether was added dropwise to that mixture over 10 minutes. The final mixture was stirred 30 minutes at −78° C., 90 minutes at 20) C. and 30 minutes at 0° C. It was then quenched by the addition of 20 ml of 20% aqueous ammonium sulfate and then poured into 50 ml of 20% aqueous ammonium sulfate. It was mixed well, and the phases were separated. The aqueous phase was extracted with ether (2 × 50 ml). Combined extracts were washed with 50 ml of cold 2% aqueous sulfuric acid. The wash solution again was extracted with ether (2 × 50 ml). Combined extracts were filtered through infusorial earth (CELITE®) and then washed with saturated aqueous sodium sulfate and brine. They were dried (MgSO$_4$) and evaporated in vacuo to yield 0.952 g of residue. That residue was dissolved in 6 ml of acetic acid-water-tetrahydrofuran (65:35:10) and stirred overnight under argon at room temperature. The solvents were removed by evaporation in vacuo; the residue was mixed with 50 ml of saturated aqueous sodium bicarbonate and extracted with 3 × 30 ml of ether-ethyl acetate (1:1). Combined extracts were washed with 50 ml of brine, dried (MgSO$_4$), and then evaporated in vacuo to yield 0.751 g of crude prostaglandin analogues. That crude product was chromatographed on silicic acid CELITE (85:15) using benzene-ethyl acetate gradient elution to yield 96.9 mg of TR 4086 and 89.9 mg of TR 4087.

Physical Chemical Data

TR 4086 — IR(CHCl$_3$): — 3600-3200, 2950, 1740 cm$^{-1}$;
NMR(CDCl$_3$): —δ 0.8(3H, s); 0.9(3H, s); 1.0–2.8 (20H, m); 3.6(3H, s); 3.9-4.3(4H, s); and 5.5 ppm(1H, bs)
TR 4087 — IR(CHCl$_3$): — 3600-3200, 2950, 1740cm$^{-1}$;
NMR(CDCl$_3$): — δ 0.8(3H, s); 0.9(3H, s); ~0.9-2.7 (20H, m); 3.4(2H, m); 3.6(3H, s); 3.9–4.2(2H, m); and 5.5 ppm(1H, bs).

EXAMPLE 5

2α-(6′-Carbomethoxyhexyl)-3β-(2″-Methyl-3″β-Hydroxycyclopent-1″-en-1″-yl)-4α-Hydroxycyclopentanone (TR 4164).

Use of 1-bromo-2-methyl-3-(1′-ethoxyethoxy)cyclopent-1-ene (2.21 mol) in the procedure outlined in either Example 1 or 2 yields 28.2 g of the title compound.

Physical Chemical Data:

Optical Rotation, [α]$_D^{25}$ + 10.4 (c 1.4, CHCl$_3$).

EXAMPLE 6

2α-(6′-Carbomethoxyhexyl)-3β-(Cyclohex-1′-en-1″-yl)-4α-Hydroxycyclopentanone (TR 4417).

Use of 1-bromo-cyclohex-1-ene in the synthetic scheme described in either Example 1 or 2 yielded the title compound.

Physical Chemical Data:

NMR(CDCl$_3$): —δ 1.1-3.1(25H, complex m); 3.7(3H, bs); 4.2(1H, m); 5.8(1H, bt, J-6Hz).
IR(CHCl$_3$): —3650(sharp), 361-3300(broad), 3000, 2925, 2850, 1740, 1725, 1440, 1320, 1100, 1070, 915, 880, 830cm$^{-1}$.
Mass Spectrum (70 eV) m/e: 322(parent), 304(p-H$_2$O), 291(p-OMe), 286(p-2H$_2$O), 278, 273, 272, 94(base peak).
Optical Rotation: [α]$_D$ −59.5° (c 1.00, CHCl$_3$).

EXAMPLE 7

2α-(6′-Carboethoxy-cis-2-Hexenyl)-3β-(Cyclododec-1″-en-1″-yl)-4α-Hydroxycyclopentanone (TR 4467).

Use of 1-bromo-cyclododec-1-ene and 2-(6′-carboethoxy-cis-2-hexenyl)-4α-(Tetrahydropyranyloxy)-cyclopent-2-enone in the procedure outlined in Examples 1 or 2 yields the title compound.

Physical Chemical Data

NMR(CDCl$_3$): — δ 1.2(3H, t, J = 7Hz); 1.2-3.1(33H, complex m); 4.2(3H, bq, J=7Hz); 5.5(3H, m).

IR(CHCl$_3$): — 3570(sharp), 3460(broad), 3000, 2930, 2850, 1735, 1710, 1460, 1440, 1375, 1150, 1080, 1070, 1015, 880, 850, 830, 810 cm$^{-1}$.

Mass Spectrum (70 eV) m/e: 418(parent), 389(p-C$_2$H$_5$), 388(p-C$_2$H$_6$), 372(p-HOC$_2$H$_5$), 371, 353, 342, 234(base peak, p-H$_2$O-C$_{12}$H$_{22}$).

Optical Rotation: [α]$_D$ −15.6° (c 1.04, CHCl$_3$).

Examples 8-16 represent preferred embodiments of analogues of 11-deoxy derivatives of the E- family of prostaglandins and are specific compounds having structure IIIc, described in the preceding SUMMARY OF THE INVENTION.

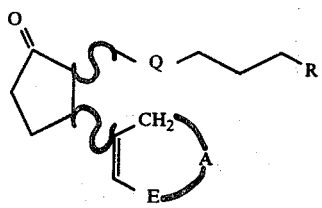

EXAMPLES 8-9:

2α-(6'-Carboxyhexyl)-3β-(3''-hydroxycyclohex-1''-en-1''-yl)-Cyclopentanone (TR 4029), 2β-(6'-Carboxyhexyl)-3α-(3''-Hydroxycyclohex-1''-en-1''-yl)-Cyclopentanone (TR 4030).

A solution of 1.08 g (4.35 mmol) of 1-bromo-3-(1'-ethoxyethoxy)-cyclohex-1-ene in 25.0 ml ether was cooled to −78° C. under argon atmosphere. Then 7.05 ml of 1.23 M t-butyllithium in n-pentane was added, and the mixture was stirred at −78° C. for 2.75 hours. A solution of 565 mg of copper-1-pentyne and 1.57 ml of hexamethyl-phosphorous triamide in 14.5 ml ether was added to the reaction flask with stirring at -78° C. The resulting mixture was stirred for 15 minutes at −78° C., and 852 mg (4.25 mmol) of 2-(6'-carbomethoxyhexyl)-2-cyclopenten-1-one in 14.5 ml ether was added thereto. The final reaction mixture was stirred for 30 minutes at −78° C. and subsequently brought to 0° C. over a period of 1.5 hours by means of an ice-salt bath. It was stirred for 0.5 hour at 0° C. and an additional 0.5 hour at 25° C. It then was processed successively with 20% aqueous (NH$_4$)$_2$SO$_4$, 2% (v/v) aqueous H$_2$SO$_4$, 5% aqueous NaHCO$_3$, saturated aqueous NaCl; then dried, filtered, and stripped to yield 1.61 g of a yellow oil. NMR(CDCl$_3$) analysis showed: δ 3.63, CO$_2$CH$_3$; and no signal corresponding to the 2-(6'-carbomethoxyhexyl)-2-cyclopenten-1-one olefinic proton. The ethoxyethoxy group was removed by reacting the oil with 30 ml of acetic acid/water (65/35), and THF for 1 hour at 25° C; 1.20 g of oil was obtained after processing as described. The ester group was hydrolyzed with 12.0 ml of 1N NaOH and 12.0 ml THF to yield 910 mg of a yellow oil which was chromatographed on silicic acid and infusorinal earth (Celite®) (85:15) to yield 151 mg of TR 4030. TR 4030 had the following special properties:

IR: λ$_{max}^{CHCl_3}$ 2.78μ, 5.78μ, 5.85μ, and 1.10μ.
MS: 308, 290, 272.

NMR(COCl$_3$): — δ 4.30, multiplet, 1H, CHOH — δ 5.60, multiplet, 1H, =CH —δ 7.40, multiplet, 2H, CO$_2$H, OH

EXAMPLE 10-11

2α-(6'-Carboxyhexyl)-3α-(3''-Hydroxy-5'',5''-Dimethyl Cyclohex-1''-en-1''-yl)Cyclopentanone (TR 4085)

2α-(6'-Carboxyhexyl)-3β-(3''-Hydroxy-5'',5''-Dimethyl-Cyclohex-1''-en-1''-yl)Cyclopentanone (TR 4084).

A solution of t-butyllithium in pentane (3.4 ml., 5.8 mmol, 1.7 M) was added dropwise to 857 mg (2.9 mmol) of 1-bromo-3-(1'-ethoxyethoxy)-5,5-dimethyl-cyclohexene in 12 ml of dry ether was stirred at −78° C. under argon atmosphere. The resulting solution was stirred for 2 hours at −78° C. It was added via polyethylene tubing to coper(I)pentyne (383 mg, 2.95 mmol) in 4 ml of dry ether with 0.83 ml of dry hexamethylphosphoroustriamide. That reaction mixture was cooled to −78° C. under argon atmosphere and was stirred for 30 minutes. A solution of 0.600 g (2.18 mmol) of 2-(6'-carbomethoxyhexyl)-cyclopent-2-enone in 2 ml of dry ether was then added dropwise to the reaction mixture over a 10 minutes period. The final mixture was stirred for 30 minutes at −78° C., 90 minutes at −20° C., and then 30 minutes at 0° C. It was then quenched by the addition of 10 ml of 20% aqueous ammonium chloride at 0° C. and then poured into 50 ml of 20% ammonium chloride, and was mixed well; the phases were then separated. The aqueous phase was extracted with ether (3 × 50 ml). Combined extracts were washed with 30 ml of cold 2% sulfuric acid, and the aqueous wash again was extracted with ether (2 × 50 ml). Combined extracts were filtered through infursorinal earth (CELITE ®) and then washed with saturated sodium bicarbonate solution and brine. The extracts were dried (MgSO$_4$) and evaporated in vacuo to yield 1.12 g of residue. That residue was stirred with 25 ml of acetic acid-water-tetrahydrofuran (65:35:10) for 1.5 hours under argon atmosphere. Solvents were removed by evaporation in vacuo; the residue was mixed with 50 ml of water and then extracted with ether-ethyl acetate (1:1; 3 × 50 ml). The combined extracts were washed 50 ml of saturated aqueous sodium bicarbonate and brine, dried (MgSO$_4$), and then evaporated in vacuo to yield 0.930 g of crude prostaglandin methyl esters. The crude ester was mixed with 50 ml of 5% potassium hydroxide in methanol-water (3:1) and stirred for 2.5 hours under nitrogen. The solvent was removed by evaporation in vacuo, and the residue was dissolved in 30 ml of water and then extracted with ether acetate (3 × 50 ml). Those combined extracts again were washed with water (2 × 50 ml). The remaining organic phase was discarded. Combined aqueous phases were acidified with 30 ml of 10% aqueous hydrochloric acid and then extracted with ether (3 × 50 ml). Those combined extracts were washed with 50 ml of brine, dried (MgSO$_4$), and evaporated in vacuo to yield 589 mg of crude prostaglandin analogues. That crude product was purified by chromatography on silicic acid-CELITE ®(85:15) using benzene-ethyl acetate gradient elution yielding 90.4 mg of TR 4085 and 92.3 mg of TR 4084.

Physical Chemical Data

TR 4084 — NMR(CDCl$_3$): δ 0.8(3H, s); 0.95(3H, s); 0.90-2.6 (22H, m); 4.1-4.4(1H, m), 5.55(1H, bs); and 6.1 ppm(2H, bs).

TR 4085 — IR(CHCl$_3$): — (2940, 1730, 1710cm$^{-1}$.
NMR(CDCl$_3$): — δ 0.8(3H, s); 0.95(3H, s); 1.1-2.8 (22H, m); 4.1-4.4-(1H, m); 5.5(1H, bs); and 6.2 ppm(2H, bs).

EXAMPLE 12 dl-2α-(6'-Carbomethoxyhexyl)-3β-(cyclohept-1"-en-1"-yl)-Cyclopentanone (TR 4296).

Substituted of 1-bromo-cyclohept-1-ene and omitting hydrolysis of the product with acid in the procedure given in the preceding example provided the title compound.

Physical Chemical Data

NMR(CDCl$_3$): δ 1.1-2.7(28H, complex m); 3.7(3H, s); 5.8(1H, bt, J=7Hz).

IR(CHCl$_3$): 3000, 2930, 2850, 1735, 1640, 1440, 1170, 840cm$^{-1}$.

Mass spectrum (70 eV) m/e: 320(parent); 289(p-OMe), 225, 178, 177, 95, 83(base peak).

EXAMPLE 13 dl-2α-(6'-Carboxy-Cis-2-Hexenyl)-3β-(cyclohex-1"-en-1"-yl)Cyclopentanone (TR 4431).

A solution of 1.11 g (9.5 mmol) 1-chloro-1-cyclohexene in 20 ml anhydrous diethyl ether was added to 0.656 g (95 mmol) of finely cut lithium wire (1% sodium) in 10 ml anhydrous ether at 0° C. and under an argon atmosphere. After addition was complete, the mixture was heated to reflux and stirred overnight. In the following morning, the mixture was cooled to room temperature, and solid material was allowed to settle out of solution. The supernatent liquid was transferred (under argon atmosphere) into a flame dried flask. Aliquots were taken of the resultant solution and titrated with 0.100 M hydrochloric acid. The amount of 1-lithio-1-cyclohexene obtained was 0.12 N.

A solution containing 39 mg (3 mmol) of copper(I)-pentyne, 0.7 ml hexamethylphosphorous triamide and 20 ml diethyl ether was added to 11 ml of 0.12 N 1-lithio-1-cyclohexene in diethyl ether (1.32 mmol) at 78° C. and under argon atmosphere. The mixture was stirred for 10 minutes at −78° C.

A solution containing 289 mg (1.3 mmol) of 2(6-carbomethoxy-cis-2-hexenyl)-2-cyclopentenone in 5 ml anhydrous toluene was added to that mixture by syringe. The resulting slurry at −78° C. for 10 minutes and gradually warmed to −20° C. over a 1.5 hour period. The slurry was quenched at −20° C. with 5 ml of 20% aqueous ammonium chloride (buffered to pH 8 with ammonium hydroxide). The layers were separated, and the organic phase was washed with 10 ml of 2% aqueous sulfuric acid. The contents of the separatory funnel were vacuum filtered (water aspirator) through a sintered glass funnel containing a pad of infusorinal earth (CELITE®). The organic phase of the filtrate was separated and washed with brine. Solvents were removed by evaporation in vacuo (water aspirator), and an orange residue was hydrolyzed to the acid by treatment with 5 ml of 5% potassium hydroxide in 3:1 (v/v) methanol-water (3 hours at room temperature). The solution was reduced in volume (rotoevaporator) and the residue was diluted with water and ether. The layers were separated and the organic phase was washed with water. The organic phase was discarded and the combined aqueous layers were diluted with ether and acidified (pH 2) with 6M hydrochloric acid. The layers were separated and the aqueous phase was back-extracted with 2 × 25 ml portions of 1:1 (v/v) ether-ethyl acetate. The combined organic layers were washed with saturated brine solution and dried (MgSO$_4$). The solvents were removed by evaporation in vacuo to yield 315 mg of the crude E prostaglandin analogue as an orange oil. This material was purified by column chromatography (80% silicic acid-20% CELITE) using benzene-ethyl acetate (gradient elution) as the eluting solvent. In this manner 126 g (34%) of dl-2α-(6 -carboxy-cis-2-hexenyl)-3β-(1-cyclohexenyl)-cyclopentanone was obtained in the form of a yellow oil.

Physical Chemical Data

NMR(CDCl$_3$): δ 1.3-2.9 (22H, complex m); 5.5(3H, complex m); 9.9(1H, bs).

IR(CHCl$_3$): 3600-3000(broad), 3000, 2925, 2850, 2830, 1735, 1710, 1440, 1410, 1285, 1140, 970, 915, 850, 830cm$^{-1}$.

Mass Spectrum (70 eV) m/e: 290(parent), 272(o-H$_2$O), 203, 195, 189, 192, 164(base peak).

EXAMPLE 14:

dl-2α-(6'-Carboxy-Cis-2-hexenyl)-3β-(Cyclooct-1"-en-1"-yl)Cyclopentanone (TR 4435).

Substitution of 1-chloro-cyclooct-1-ene for 1-chloro-cyclohex-1-ene in the preceding example yielded the title compound.

Physical Chemical Data

NMR(CDCl$_3$): δ 1.3-2.9(26H, complex m); 5.5 (3H, m); 8.1(1H, bs).

IR(CHCl$_3$): 3600-3000(broad), 2924, 2850, 2830, 1735, 1710, 1440, 1410, 1280, 1225, 1140, 970, 855, 825cm$^{-1}$.

Mass Spectrum (70 eV)m/e: 318(parent), 300(p-H$_2$O), 290, 272, 244, 243, 292(base peak, p-C$_7$H$_{10}$O$_2$).

EXAMPLES 15–16 dl-2α-(6'-Carboxy-2'-hexenyl)-3β-(3"-Hydroxyclohex-1"-en-1"-yl)cyclopentanone (TR 4130), dl-2β(6'-Carboxy-2'hexenyl)-3α-(3"-Hydroxycyclohex-1"-en-1"-yl)cyclopentanone (TR 4131).

Use of 1-bromo-3-(1'-ethoxyethoxy)cyclohex-1-ene in lieu of 1-chloro-cyclohex-1-ene in example 13 yielded the title compounds.

Physical Chemical Data

TR 4130 —NMR(CDCl$_3$): 1.2—3.0(2H, m); 4.3(1H, m); 5.4(2H, m); 5.6(1H, m); 7.07 ppm(2H, bs).

IR(CHCl$_3$): 970, 1210, 1740, 2960, 2800—3000cm$^{-1}$

Mass Spectrum (70 eV) m/e: 306(parent); 288(p-H$_2$O).

TR 4131 —NMR(CDCl$_3$): 1.2—3.0(2H, m); 4.3(1H, m); 5.4(2H, m); 5.6(1H, m); 7.07 ppm(2H, bs).

IR(CHCl$_3$): 970, 1210, 1740, 2960, 2800—3000cm$^{-1}$.

Mass Spectrum(70 eV) m/e: 306(parent); 288(p-H$_2$O).

Examples 17–20 are preferred embodiments of analogues of prostaglandins of the F- class and have the structure IIId described in the preceding SUMMARY OF THE INVENTION.

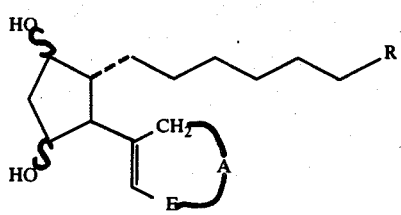
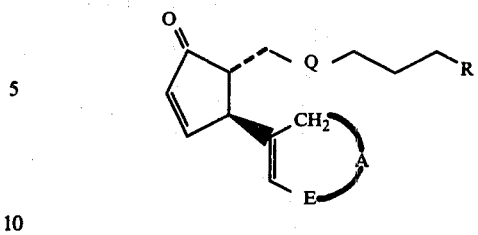

EXAMPLES 17—18

1β-Hydroxy-2β-(6'-Carbomethoxyhexyl)-3"α-Hydroxycyclohex-1"-en-1"yl)-4α-Hydroxy-Cyclopentane (TR 4203), and 1α-Hydroxy 2α-(6'-Carbomethoxyhexyl)-3β-(3"α-Hydroxycyclohex-1"-en-1"-yl)-4α-Hydroxycyclopentane (TR 4165).

While a solution of 26.7 mg of 2α-(6-carbomethoxyhexyl)-3β-(3"α-hydroxycyclohex-1"-en-1"-yl)-4α-hydroxycyclopentanone in 15 ml of dry methanol was stirred in a methanol-ice bath, 21 mg of sodium borohydride was added in portions. The resulting mixture was stirred for 20 minutes in the cold bath and then for 1 hours at room temperature. The solvents were removed by evaporation in vacuo and the residue was dissolved in water and extracted several times with ether-ethyl acetate (1:1). The combined extract was washed with brine, dried (MgSO₄), and evaporated in vacuo. The residue was chromatographed on silicic acid-CELITE ® (85:15) using benzene-ethyl acetate gradient elution to give 6.7 mg of TR 4165 and 13.6 mg of TR 4203.

Physical Chemical Data.

TR 4203 — IR(CHCl$_3$): 3600—3200, 2940, 1730, 1440, 1170 and 1070cm$^{-1}$.

NMR(CDCl$_3$): δ0.8—2.6(25H, m); 3.68(3H, s); 4.1(3H, broad m); and 5.6 ppm(1H, m).

Optical Rotation: [a]$_D$ −44.2°(c 1.36, CHCl$_3$).

TR 4165: IR and NMR as above.

Optical Rotation: [a]$_D$ +46.7°(c 0.34, CHCl$_3$).

Examples 19—20

1β-Hydroxy-2α-(6'-Carbomethoxyhexyl)-3β-(3"β-Hydroxycyclohex-1"-en-1"-yl)-4α-Hydroxycyclopentane (TR 4123), and 1α-Hydroxy-2α-(6'-Carbomethylhexyl)-3β-(3"β-Hydroxycyclohex-1"-en-1"-yl)-4α-Hydroxycyclopentane (TR 4122).

Use of 2α-(6'-Carbomethoxyhexyl)-3β-(3"-β-Hydroxycyclohex-1"-en-1"-yl)-4α-Hydroxycyclopentanone in lieu of 2α-(6'-carbomethoxyhexyl)-3β-(3"α-hydroxycyclohex-1"-en-1"-yl)-4α-hydroxycyclopentanone in the procedure given in examples 17–18 yielded the title compounds.

Physical Chemical Data

TR 4123 — IR, NMR, same as for TR 4203.
Optical Rotation: [a]$_D$ − 28.6° (c 1.70, CHCl$_3$).
TR 4122 — IR, NMR, same as for TR 4203.
Optical Rotation: [a]$_D$ +0.75(c 1.04, CHCl$_3$).

Examples 21–24 are preferred embodiments of analogues of natural prostaglandins of the A- family and are represented by structure IIIα which is described in the preceding SUMMARY OF THE INVENTION:

EXAMPLES 21-22

2α-(6'-Carbomethoxyhexyl)-3β-(3"α-Hydroxycyclohex-1"-en-1"-yl)-cyclopent-4-enone (TR 4148), and 2α-(6'-Carbomethoxyhexyl)-3β-(3"-β-Hydroxycyclohex-1"-en-1"-yl)-cyclopent-4-enone (TR 4149).

A solution of 2α-(6'-carbomethoxyhexyl)-3β-(3"α-hydroxycyclohex-1"-en-1"-yl)-4α-hydroxycyclopentanone (93.9 mg) in 6 ml of acetic acid and 1 ml of water was heated at 60° under nitrogen for 18 hours. Solvents were removed by evaporation in vacuo. Water was added to the reaction mixture which was then extracted twice with ether-ethyl acetate (1:1). Combined extracts were washed with water, saturated aqueous sodium bicarbonate, and brine. They were dried (MgSO₄) and evaporated in vacuo yielding 57 mg of crude prostaglandin analogues. That product was purified by chromatography on silicic acid infusori nal earth (CELITE ®) (85:15) using benzene-ethyl acetate gradient elution to obtain 21.4 mg of TR 4148.

A 48.6 mg portion of 2α-(6'-carbomethoxyhexyl)-3β-(3"α-hydroxycyclohex-1"-en-1"-yl)-4α-hydroxycyclopentanone was similarly treated to yield 13.3 mg of TR 4149.

Physical Chemical Data.

TR 4149 — NMR(CDCl$_3$): δ0.8-3.6(21H, m); 3.7(3H, s); 4.1(1H, bs); 5.5(1H, m); 6.2(1H, m); and 7.5 ppm (1H, m).

IR(CHCl$_3$): 1705, 1730, 2940 and 3200-3600cm$^{-1}$.

TR 4148 — NMR(CDCl$_3$): δ0.8-2.6(21H, m); 3.7(3H, s); 4.1(1H, bs); 5.5(1H, m); 6.2(1H, m); and 7.5 ppm (1H, m).

IR(CHCl$_3$): 1705, 1730, 2940 and 3200-3600cm$^{-1}$.

EXAMPLE 23

2α-(6'-Carbomethoxyhexyl)-3β-(Cyclohex-1"-en-1"-yl)-Cyclopent-4-enone (TR 4418).

The procedure outlined in the preceding examples yielded the title compound when 2α-(6'-carbomethoxyhexyl)-3β-(cyclohex-1"-en-1"-yl)-4α-hydrroxycyclopentanone was used as the starting material.

Physical Chemical Data

NMR(CDCl$_3$): δ1.1-2.6(21H, complexm); 3.2(1H, m); 3.7(3H, s); 5.6(1H, m); 6.3(1H, dd, J=7,2Hz); 7.6(1H, dd, J=7,2Hz).

IR(CHCl$_3$): 3000, 2930, 2850, 1725, 1700, 1590, 1435, 1340, 1170, 1075, 915, 830, 810cm$^{-1}$.

Mass Spectrum (70 eV) m/e: 304(parent), 273(p-OMe), 272)p-HOMe), 244, 192, 175, 162(base peak).

Optical Rotation: [α]$_D$ +125.9° (c 1.00, CHCl$_3$).

EXAMPLE 24

2α-(6'-Carbomethoxy-Cis-2-Hexenyl)-3β-(Cyclododec-1''-en-1''-yl)-Cyclopent-4-enone (TR 4466).

The procedure outlined in the preceding examples 21-23 yielded the title compound when 2α-(6'-carbomethoxyhexyl)-3β-(cyclododec-1''-en-1''-yl)-4α-hydroxycyclopentanone was used as a starting material.

Physical Chemical Data

NMR(CDCl$_3$): δ1.2(3H, t, J=7Hz); 1.2-3.1(29H, complex m); 3.6(1H, dd, J=7,7Hz); 4.2(2H, q, J=7Hz); 5.5(3H, m); 6.3(1H, dd, J=5.2Hz); 7.75(1H, dd, J=5,2Hz).

IR(CHCl$_3$): 2980, 2920, 2840, 1715, 1705, 1590, 1460, 1440, 1375, 1175, 1150, 1085, 1015, 885, 850, 810cm$^{-1}$.

Optical Rotation: [α]$_D$ +32.3° (c 1.28, CHCl$_3$).

EXAMPLE 25

A. Evaluation of Inhibition of Human Platelet Aggregation by Analogues of Prostaglandins Human Structure III.

The ability of test compounds to inhibit platelet aggregation was determined by a modification of the turbidometric technique of Born (Nature, 194: 927 [1962]). Blood was collected from human volunteers who had not ingested aspirin or aspirin-containing products within the preceding two weeks in heprinized containers and was allowed to settle for one (1) hour. The platelet rich plasma (prp) supernates were collected and pooled. Siliconized glassware was used throughout.

In a representative assay 1.9 ml of PRP and 0.2 ml of test compound at the appropriate concentratsion (0.001 to 100 mcgm), or 0.2 ml of distilled water (control procedure) were placed in sample cuvettes. The cuvettes were placed in a 37° C. incubation block for 15 minutes, and then in a spectrophotometer linked to a strip chart recorder. After 30-60 seconds, 0.2 ml of a solution, prepared by diluting a calf-skin collagen solution 1:9 with Tyrodes'Solution, was added to each cuvette. Platelet aggregation was evidenced by a decrease in optical density.

Calculation of the degree of inhibition of platelet agreegation exhibited by each concentration of test compound was accomplished according to the method of Caprino et al., (Arzneim-Forsch., 23: 1277 [1973]). An ED$_{50}$ value was then determined graphically. Activity of the compounds was scored as follows:

| ED$_{50}$(mcg/kg) | Activity Value |
|---|---|
| >1.0 | 1 |
| >0.1 <1.0 | 2 |
| >0.1 ≦0.1 | 3 |

B. Evaluation of the Effects of Prostaglandin Analogues III on Blood Pressure and Heart Rate in the Anesthetized Cat.

The acute effect of test compounds on blood pressure and heart rate were determined in cats of either sex anesthetized with a mixture of pentobarbital sodium (35 mg/kg, i.v.) and barbital sodium (100 mg/kg, i.v.). Cannulas were placed in the trachea to allow adequate spontaneous ventilation, in a femeral artery for blood pressure recording with a strain gage transducer, and a saphenous vein for drug administration. Heart rate was recorded by means of a cardiotachometer driven by the R wave of the electrocardiogram. After a period of 10 minutes of stable recordings of blood pressure and heart rate, the test compound was administered intravenously at doses increasing from 0.01 to 10.0 mcg/kg, spaced one log and injected at 10 minute intervals. All doses were injected in a volume of 0.1 ml/kg. Modifications of blood pressure and heart rate induced by the test compound were expressed both in absolute units (mmHg and beats/minutes) and as percent of values recorded immediately before administration of each dose. Biphasic responses were tabulated in the order in which they occur. The direction of the observed changes was also noted (+ for increases and - for decreases).

Activity of compounds in this test ws judged only on the basis of the degree of hypotension observed. Thus, the ED$_{50}$ mmHg (dose decreasing blood pressure by 50 mmHg) was calculated graphically and the compound scored according to the following scale:

| ED$_{50}$ mmHg, mcg/kg | Activity Value |
|---|---|
| >1.0 | 1 |
| 1.01 - 10.0 | 2 |
| 0.11 - 1.0 | 3 |

C. Evaluation of the Effects of Prostaglandin Analogues III on Blood Pressure in the Hypertensive Rat.

The acute antihypertensive activity of test compounds was determined in rats made hypertensive by the procedure of Groolman (Proc. Soc. Exper. Biol. Med., 57:102 [1944]). Female rats weighing between 60 and 100 g were anesthetized with ether, the right kidney approached through a flank retroperitoneal incision, decapsulated and tied with a figure-of-eight ligature. The animals were left to recover and two weeks later were again anesthetized and the contralateral kidney removed. Four weeks after the second operation the rats were subjected to indirect blood pressure measurements and those showing systolic pressure values greater than 160 mmHg were selected for drug testing.

Blood pressure was measured in the tail with an inflatable occluding cuff placed at the base of the extremity and a pulse detector located distally. The cuff was inflated to approximately 300 mmHg and was slowly deflated until pulsations appeared, indicating the level of systolic pressure; diastolic pressure ws not recorded by this procedure. All measurements were carried out in unanesthetized, unsedated animals maintained in a warm environment during the recording procedure and for at least 6 hours before. In all cases, three pressure readings were obtained in succession and mean values were calculated thereof.

Experiments were carried out in groups of five hypertensive rats in which systolic pressure was determined immediately before and 2, 4, 6 and 8 hours after the intraperitoneal administration of the test compound at a dose of 1 mg/kg. Drugs were diluted from stock solutions with phosphate buffer (Lee et al., Prostaglandins 3:29 [1973]), so as to inject this quantity in a volume of 1 ml/kg. Changes from control blood pressure values were calculated for each interval both in mmHg and in percent, and evaluated for significance by means of Wilcoxon's signed rank test (Wilcoxon and Wilcox, Some Rapid Approximate Statistical Procedures, Lederle Laboratories, Pearl River [1964]). Activity of the compound was scored as follows:

| Blood pressure decrease | Activity Value |
|---|---|
| Active, but not significant at any time interval | 1 |
| Significant at one time interval | 2 |
| Significant at two time intervals | 3 |

Table D summarizes the results of the preceding assays utilizing the preferred examples.

TABLE D

Summary of Activity of Prostaglandin Analogues III in: Inhibition of Human Platelet Aggregation; Effects on Feline Normal Blood Pressure and Heart Rate; and, Effects on Rodent Hypertension

| | | Activity Value | | |
|---|---|---|---|---|
| TR No. | Example No. | Inhibition of Platelet Aggregation | Decrease in Normal Feline Blood Pressure | Rodent Hypertension |
| 4148 | 21 | NT | 1 | NT |
| 4149 | 22 | NT | 1 | NT |
| 4418 | 23 | 1 | NT | 1 |
| 4466 | 24 | 1 | NT | NT |
| 4082 | 1 | NT | 1 | 2 |
| 4083 | 2 | NT | 1 | NT |
| 4086 | 3 | NT | 1 | NT |
| 4087 | 4 | 1 | 1 | NT |
| 4164 | 5 | 1 | 1 | NT |
| 4029 | 8 | 1 | 1 | 1 |
| 4030 | 9 | 1 | 1 | 1 |
| 4084 | 11 | 1 | 1 | NT |
| 4085 | 10 | 1 | 1 | NT |
| 4296 | 12 | 1 | NT | 3 |
| 4417 | 6 | 1 | 1 | 1 |
| 4130 | 15 | 1 | 1 | 1 |
| 4131 | 16 | 1 | 1 | 1 |
| 4431 | 13 | 1 | NT | 1 |
| 4435 | 14 | 1 | NT | 1 |
| 4467 | 7 | 1 | NT | NT |
| 4122 | 20 | 1 | NT | NT |
| 4165 | 18 | NT | 2 | NT |
| 4123 | 19 | 1 | 3 | NT |

TABLE D-continued

Summary of Activity of Prostaglandin Analogues III in: Inhibition of Human Platelet Aggregation; Effects on Feline Normal Blood Pressure and Heart Rate; and, Effects on Rodent Hypertension

| | | Activity Value | | |
|---|---|---|---|---|
| TR No. | Example No. | Inhibition of Platelet Aggregation | Decrease in Normal Feline Blood Pressure | Rodent Hypertension |
| 4203 | 17 | 1 | NT | NT |

NT = Not Tested.

What is claimed is:

1. A compound having the formula,

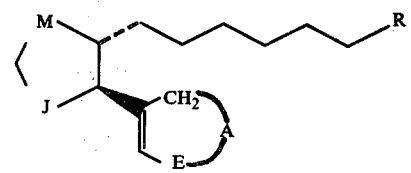

in which:
A is selected from the group consisting of methylene, ethylene, 1,1,-dimethylethylene, trimethylene, tetramethylene, pentamethylene, hexamethylene, hepamethylene, and octamethylene;
E is selected from the group consisting of methylene, α-hydroxymethylene, and β-hydroxymethylene;
J is selected from the group consisting of α-hydroxymethylene and β-hydroxymethylene;
M is selected from the group consisting of α-hydoxymethylene and β-hydroxymethylene; and
R is selected from the group consisting of carboxyl, carbomethoxy, and carbethoxy.

2. The compound as in claim 1, 1α-hydroxy-2α-(6'-carbomethoxyhexyl)-3β-(3"β-hydroxycyclohex-1"-en-1"-yl)-4α-hydroxycyclopentane.

3. The compound as in claim 1, 1α-hydroxy-2α-(6'-carbomethoxyhexyl)-3β-(3"α-hydroxycyclohex-1"-en-1"-yl)-4α-hydroxycyclopentane.

4. The compound as in claim 1, 1β-hydroxy-2α-(6'-carbomethoxyhexyl)-3β-(3"β-hydroxycyclohex-1"-en-1"-yl)-4α-hydroxycyclopentane.

5. The compound as in claim 1, 1β-hydroxy-2α-(6'-carbomethoxyhexyl)-3β-(3"α-hydroxycyclohex-1"-en-1"-yl)-4α-hydroxycyclopentane.

* * * * *

UNITED STATES PATENT AND TRADEMARK OFFICE
CERTIFICATE OF CORRECTION

PATENT NO. : 4,138,583

DATED : Feb. 6, 1979

INVENTOR(S) : Warren D. Woessner et al.

It is certified that error appears in the above–identified patent and that said Letters Patent are hereby corrected as shown below:

| | |
|---|---|
| Column 3, Line 36, | Change "PFG$_{60}$" to --PGF$_\alpha$--. |
| Column 3, Line 39, | Change "PGF$_{60}$" to --PGF$_\alpha$--. |
| Column 3, Line 47, | Change "PGF$_{60}$" to --PGF$_\alpha$--. |
| Column 3, Line 59, | Change "aND" to --and--. |
| Column 4, Line 3, | Change "PGE$_{60}$" to --PGF$_\alpha$--. |
| Column 4, Line 3, | Change "vasoconstrictos" to --vasconstrictors--. |
| Column 4, Line 27, | Change "Prostaglandinc" to --Prostaglandins--. |
| Column 5, Line 17, | delete the first ")" |
| Column 6, Line 55, | Change "(tetrahydropyranox-1yl)" to --(tetrahydropyranox-1-yl)--. |
| Column 6, Line 56, | Change "(ditetrahydropyranox1-yl)" to --(ditetrahydropyranox-1-yl)--. |
| Column 6, Line 60, | change "(1-cycloalken-1yl)" to --(1-cycloalken-1-yl)--. |
| Column 7, Line 7, | Change "J" to --J'--. |
| Column 7, Line 8, | Change "J" to --J'--. |

UNITED STATES PATENT AND TRADEMARK OFFICE
CERTIFICATE OF CORRECTION

PATENT NO. : 4,138,583

DATED : Feb. 6, 1979

INVENTOR(S) : Warren D. Woessner et al.

It is certified that error appears in the above-identified patent and that said Letters Patent are hereby corrected as shown below:

| | |
|---|---|
| olumn 7, Line 9, | Change "J" to --J'--. |
| olumn 7, Lines 9-13 | delete the formula and substitute therefor: |

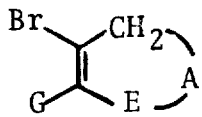

| | |
|---|---|
| olumn 7, Lines 29-35, | insert --Compound V, t-butyllithium, is commerically available or is easily prepared by methods well known in organic chemistry. Hexamethylphosphorous triamide copper iodide, VI, is prepared as follows: (1) add 18.39 g of purified--. |
| olumn 7, Line 37, | Change "arbronted" to --activated--. |
| olumn 7, Line 51, | Change "onone" to --enone--. |
| olumn 7, Line 53, | Change "onone" to --enone--. |
| olumn 7, Line 54, | Change "onone" to --enone--. |
| olumn 7, Line 56, | Change "onone" to --enone--. |

UNITED STATES PATENT AND TRADEMARK OFFICE
CERTIFICATE OF CORRECTION

PATENT NO. : 4,138,583

DATED : Feb. 6, 1979

INVENTOR(S) : Warren D. Woessner et al.

It is certified that error appears in the above–identified patent and that said Letters Patent are hereby corrected as shown below:

Column 7, Line 57,   Change "onone" to -- enone --.

Column 8, Line 65,   Change "Iva" to --IVa--.

Column 9, Line 10,   Change "cyclohex:1-ene" to --cyclohex-1-ene--.

Column 9, Line 13,   Change "Cyclodidec" to --cyclododec--.

Column 9, Line 19,   Change "en1-one"to --en-1-one--.

Column 9, Line 20,   Change "en1-one" to --en-1-one--.

Column 9, Line 36,   Change "epoxyethyoxy" to--ethoxyethoxy--.

Column 9, Line 38,   Change "cyclhex" to --cyclohex--.

Column 11, Line 37,  delete "cyclohex"

UNITED STATES PATENT AND TRADEMARK OFFICE
CERTIFICATE OF CORRECTION

PATENT NO. : 4,138,583
DATED : Feb. 6, 1979
INVENTOR(S) : Warren D. Woessner et al.

It is certified that error appears in the above-identified patent and that said Letters Patent are hereby corrected as shown below:

| | |
|---|---|
| Column 11, Line 60, | Change "20)" to --minus 20°--. |
| Column 15, Line 9, | Change "Substituted" to --Substitution--. |
| Column 15, Line 47, | insert --was stirred-- between "slurry" and "at". |
| Column 17, Line 13, | Change "2β" to --2α--. |
| Column 17, Line 13, | insert --(-- before the "3". |
| Column 18, Line 31, | Change "infusori nal" to --infusorinal--. |
| Column 18, Line 56, | Change "hydrroxycy" to --hydroxycy--. |
| Column 19, Line 34, | Change "concentratsion" to --concentration--. |

Signed and Sealed this

Nineteenth Day of June 1979

[SEAL]

Attest:

RUTH C. MASON
Attesting Officer

DONALD W. BANNER
Commissioner of Patents and Trademarks